US 11,918,753 B2

(12) United States Patent
Moquin et al.

(10) Patent No.: US 11,918,753 B2
(45) Date of Patent: *Mar. 5, 2024

(54) FLEXIBLE CATHETER

(71) Applicant: TRACTUS VASCULAR, LLC, Eatontown, NJ (US)

(72) Inventors: Craig Moquin, Fanwood, NJ (US); Andrew Filachek, Beechwood, NJ (US); Paige Reinhardt, Highlands, NJ (US); Matthew Koehler, Toms River, NJ (US); Darren De Medici, Middletown, NJ (US); Janet Burpee, Fair Haven, NJ (US)

(73) Assignee: TRACTUS VASCULAR, LLC, Eatontown, NJ (US)

( * ) Notice: Subject to any disclaimer, the term of this patent is extended or adjusted under 35 U.S.C. 154(b) by 823 days.

This patent is subject to a terminal disclaimer.

(21) Appl. No.: 16/653,373

(22) Filed: Oct. 15, 2019

(65) Prior Publication Data
US 2020/0078551 A1 Mar. 12, 2020

Related U.S. Application Data

(63) Continuation of application No. 15/515,806, filed as application No. PCT/US2016/068646 on Dec. 27, 2016, now Pat. No. 10,525,231.
(Continued)

(51) Int. Cl.
*A61M 25/01* (2006.01)
*A61B 17/22* (2006.01)
(Continued)

(52) U.S. Cl.
CPC ......... *A61M 25/0013* (2013.01); *A61B 17/22* (2013.01); *A61L 29/02* (2013.01);
(Continued)

(58) Field of Classification Search
CPC .............. A61B 17/32002; A61B 17/32; A61B 17/320016; A61B 17/22;
(Continued)

(56) References Cited

U.S. PATENT DOCUMENTS 2,515,365 A 7/1950 Zublin
5,108,411 A 4/1992 McKenzie
(Continued)

FOREIGN PATENT DOCUMENTS

CN 105142709 A 12/2015
EP 2351593 A2 8/2011
(Continued)

OTHER PUBLICATIONS

Thomas, International Search Report & Written Opinion of PCT/US2016/068646, 18 pages (dated Mar. 2017).
(Continued)

*Primary Examiner* — Katherine H Schwiker
(74) *Attorney, Agent, or Firm* — Studebaker & Brackett PC

(57) ABSTRACT

A flexible, elongated catheter tube having distal and proximal ends and a laser cut section there between. The laser cut section makes up a majority of the catheter length and is cut in a continuous helical pattern forming interlocking teeth which can be sinusoidal, triangular, square or like shapes, preferably sinusoidal. The interior of the tube has a polymeric layer which forms the internal lumen of the catheter. The exterior of the tube has a polymer coating. A short portion of the distal end is uncut and is followed by a narrower terminal section which can be tapered for better blockage penetration. The interlocking teeth disengage and reengage in a fish-scale manner without undergoing plastic deformation of the metal tube and without substantial polymer separation from the tube exterior.

8 Claims, 15 Drawing Sheets

Related U.S. Application Data

(60) Provisional application No. 62/274,203, filed on Jan. 1, 2016.

(51) Int. Cl.

| | | |
|---|---|---|
| *A61L 29/02* | (2006.01) | |
| *A61L 29/04* | (2006.01) | |
| *A61L 29/06* | (2006.01) | |
| *A61L 29/08* | (2006.01) | |
| *A61M 25/00* | (2006.01) | |
| *B23K 26/38* | (2014.01) | |
| *F16C 1/00* | (2006.01) | |
| *F16C 1/02* | (2006.01) | |
| *A61B 17/00* | (2006.01) | |
| *B23K 101/06* | (2006.01) | |
| *B23K 103/00* | (2006.01) | |

(52) U.S. Cl.
CPC .......... *A61L 29/041* (2013.01); *A61L 29/049* (2013.01); *A61L 29/06* (2013.01); *A61L 29/085* (2013.01); *A61M 25/0045* (2013.01); *A61M 25/0054* (2013.01); *A61M 25/01* (2013.01); *A61M 25/0141* (2013.01); *B23K 26/38* (2013.01); *F16C 1/00* (2013.01); *F16C 1/02* (2013.01); *A61B 2017/00309* (2013.01); *A61B 2017/00526* (2013.01); *A61B 2017/00853* (2013.01); *A61B 2017/00867* (2013.01); *A61B 2017/22038* (2013.01); *A61B 2017/22094* (2013.01); *A61L 2420/08* (2013.01); *A61M 2025/0047* (2013.01); *A61M 25/0051* (2013.01); *A61M 2205/0222* (2013.01); *A61M 2205/0238* (2013.01); *A61M 2205/0266* (2013.01); *B23K 2101/06* (2018.08); *B23K 2103/42* (2018.08); *F16C 2208/36* (2013.01); *F16C 2223/30* (2013.01); *F16C 2240/60* (2013.01); *F16C 2316/10* (2013.01)

(58) Field of Classification Search
CPC ......... A61B 2017/32002; A61B 2017/320028; A61B 2017/320032; A61B 2017/22094; A61B 2017/22095; A61B 2017/22038; A61B 2017/00867; A61M 25/0138; A61M 25/0013; A61M 25/0045; A61M 25/0054; A61M 2205/0266; A61L 29/02
See application file for complete search history.

(56) References Cited

U.S. PATENT DOCUMENTS

| | | | |
|---|---|---|---|
| 5,334,145 | A | 8/1994 | Lundquist et al. |
| 5,437,288 | A | 8/1995 | Schwartz et al. |
| 5,573,520 | A | 11/1996 | Schwartz et al. |
| 5,683,640 | A | 11/1997 | Miller et al. |
| 5,747,429 | A | 5/1998 | Katoh et al. |
| 6,053,922 | A | 4/2000 | Krause et al. |
| 6,447,518 | B1 | 9/2002 | Krause et al. |
| 6,652,508 | B2 | 11/2003 | Griffin et al. |
| 6,656,195 | B2 | 12/2003 | Peters et al. |
| 6,921,397 | B2 | 7/2005 | Corcoran et al. |
| 7,300,430 | B2 | 11/2007 | Wilson et al. |
| 7,389,148 | B1 | 6/2008 | Morgan |
| 7,413,563 | B2 | 8/2008 | Corcoran et al. |
| 7,625,364 | B2 | 12/2009 | Corcoran et al. |
| 7,708,704 | B2 | 5/2010 | Mitelberg et al. |
| 7,717,930 | B2 | 5/2010 | Paul et al. |
| 7,763,012 | B2 | 7/2010 | Petrick et al. |
| 7,879,022 | B2 | 2/2011 | Bonnette et al. |
| 8,206,370 | B2 | 6/2012 | von Oepen et al. |
| 8,206,372 | B2 | 6/2012 | Larson et al. |
| 8,323,241 | B2 | 12/2012 | Salahieh et al. |
| 8,357,140 | B2 | 1/2013 | Majercak et al. |
| 8,366,559 | B2 | 2/2013 | Papenfuss et al. |
| 8,376,865 | B2 | 2/2013 | Forster et al. |
| 8,439,947 | B2 | 5/2013 | Howard et al. |
| 8,454,535 | B2 | 6/2013 | Majercak et al. |
| 8,632,556 | B2 | 1/2014 | Jacobs et al. |
| 8,758,231 | B2 | 6/2014 | Bunch et al. |
| 9,060,806 | B2 | 6/2015 | Thatipelli |
| 9,078,740 | B2 | 7/2015 | Steiner et al. |
| 9,232,954 | B2 | 1/2016 | Steiner et al. |
| 9,233,255 | B2 | 1/2016 | Powers |
| 9,295,807 | B2 | 3/2016 | Chin et al. |
| 10,335,575 | B2 | 7/2019 | Kobayashi |
| 10,525,231 | B2 | 1/2020 | Moquin et al. |
| 2002/0038129 | A1 | 3/2002 | Peters et al. |
| 2003/0032970 | A1 | 2/2003 | Hiltebrandt |
| 2004/0106976 | A1 | 6/2004 | Bailey et al. |
| 2005/0080400 | A1 | 4/2005 | Corcoran et al. |
| 2006/0064123 | A1 | 3/2006 | Bonnette et al. |
| 2006/0084839 | A1 | 4/2006 | Mourlas et al. |
| 2006/0084939 | A1 | 4/2006 | Lentz |
| 2006/0142696 | A1 | 6/2006 | Kumoyama et al. |
| 2007/0088323 | A1 | 4/2007 | Campbell et al. |
| 2008/0147001 | A1 | 6/2008 | Al-Marashi et al. |
| 2009/0099554 | A1 | 4/2009 | Forster et al. |
| 2010/0241154 | A1 | 9/2010 | Larson et al. |
| 2010/0331776 | A1 | 12/2010 | Salahieh et al. |
| 2011/0152880 | A1 | 6/2011 | Alvarez et al. |
| 2011/0264125 | A1 | 10/2011 | Wilson et al. |
| 2012/0095485 | A1 | 4/2012 | Cully et al. |
| 2012/0143234 | A1 | 6/2012 | Wilson et al. |
| 2012/0265229 | A1 | 10/2012 | Rottenberg et al. |
| 2012/0289987 | A1 | 11/2012 | Wilson et al. |
| 2012/0303005 | A1 | 11/2012 | Forster et al. |
| 2014/0012301 | A1 | 1/2014 | Wilson et al. |
| 2014/0031843 | A1 | 1/2014 | Rottenberg et al. |
| 2014/0114288 | A1 | 4/2014 | Beasley et al. |
| 2014/0135736 | A1 | 5/2014 | Hebert |
| 2014/0148787 | A1 | 5/2014 | Forster et al. |
| 2014/0235361 | A1 | 8/2014 | Forster et al. |
| 2014/0277009 | A1 | 9/2014 | Thatipelli |
| 2014/0283355 | A1 | 9/2014 | Chin et al. |
| 2015/0094532 | A1 | 4/2015 | Wilson et al. |
| 2015/0094656 | A1 | 4/2015 | Salahieh et al. |
| 2015/0216548 | A1 | 8/2015 | Furuya et al. |
| 2015/0374398 | A1 | 12/2015 | Tobis |
| 2016/0082225 | A1 | 3/2016 | Kobayashi |

FOREIGN PATENT DOCUMENTS

| | | |
|---|---|---|
| JP | H09-294810 A | 11/1997 |
| JP | 2990070 B2 | 12/1999 |
| JP | 2007-503970 A | 3/2007 |
| JP | 2013-544561 A | 12/2013 |
| JP | 2014-519376 A | 8/2014 |
| WO | 2005/004965 A2 | 1/2005 |
| WO | 2012/158152 A1 | 11/2012 |
| WO | 2014-174661 A1 | 10/2014 |

OTHER PUBLICATIONS

Banerjee & Brilakis "Coronary chronic total occlusion interventions" American College of Cardiology, Jun. 9, 2015, 11 pages, accessed Mar. 16, 2017 at http://www.acc.org/latest-in-cardiology/articles/2015/06/09/13/31/coronary-chronic-total-occlusion-interventions.

Javed & Laird "Specialty crossing devices: Understanding the learning curve" Endovascular Today, 52-57 (May 2012).

Prashant "Current and emerging catheter technologies for percutaneous transluminal coronary angioplasty" Research Reports in Clinical Cardiology, 2014:5, 213-226 (Sep. 2014).

Sianos et al. "Theory and practical based approach to chronic total occlusions" BMC Cardiovascular Disorders, 16:33, 11 pages (Feb. 2016).

US. Food and Drug Administration. 510(k) Summary. K072724.

(56) References Cited

OTHER PUBLICATIONS

Nov. 9, 2007. 5 pages. Searchable 510(k) Database. Web Accessed Mar. 24, 2017. <http://www.accessdata.fda.gov/cdrh_docs/pdf7/K072724.pdf>.

US. Food and Drug Administration. 510(k) Summary. K033678. Feb. 23, 2004. 5 pages. Searchable 510(k) Database. Web Accessed Mar. 24, 2017. <http://www.accessdata.fda.gov/cdrh_docs/pdf7/K033678.pdf>.

US. Food and Drug Administration. 510(k) Summary. K133539. Mar. 26, 2014. 7 pages. Searchable 510(k) Database. Web. Accessed Mar. 24, 2017. <http://www.accessdata.fda.gov/cdrh_docs/pdf7/K133539.pdf>.

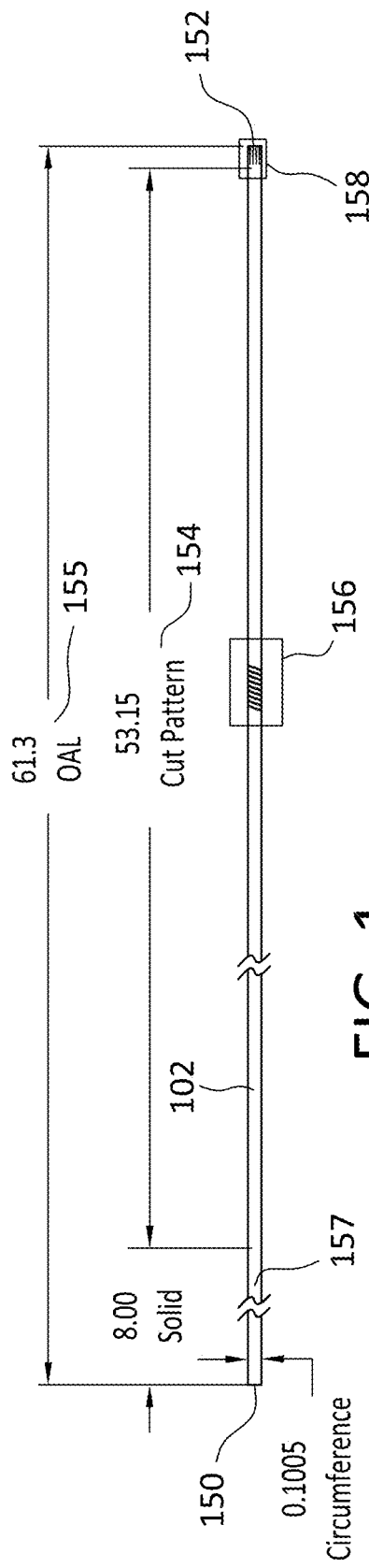
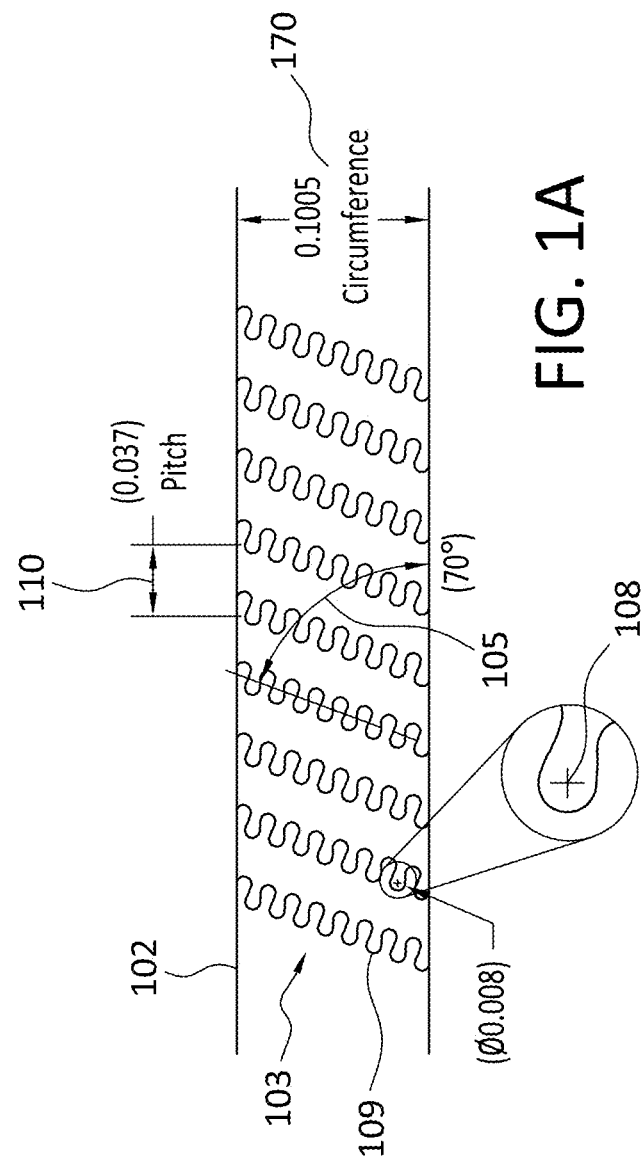
FIG. 1
FIG. 1A

FLEXIBLE CATHETER

CROSS-REFERENCE TO RELATED APPLICATIONS

This is a continuation of application Ser. No. 15/515,806, filed Mar. 30, 2017, now U.S. Pat. No. 10,525,231; which is the U.S. national stage of Application No. PCT/US2016/068646, filed Dec. 27, 2016; which claims priority benefit of Provisional Application No. 62/274,203, filed Jan. 1, 2016; the entire contents of which are hereby incorporated herein by reference.

FIELD OF THE INVENTION

This invention relates to a flexible catheter tube which is capable of transmitting rotary and axial motion to resolve blockages in a body lumen such as a blood vessel.

BACKGROUND

For well over fifty years, there has been a need to create a flexible tube from an otherwise stiff tube by cutting the tube along the length. There are many examples of this design approach for many instruments in medical devices including catheters and guidewires (U.S. Pat. No. 5,573,520), bone reamers (U.S. Pat. Nos. 5,108,411 and 6,053,922) and other non-medical applications such flexible drill bores for well drilling (U.S. Pat. No. 2,515,365).

Flexible shafts and couplings are used to transmit rotary power between a power source and a driven part when a straight, unobstructed path is unavailable. A flexible shaft generally consists of rotating shaft with end fittings for attachment to mating parts which together construct a device. The power source is anything which can transmit the correct forces including a motor or a physician's hand. The shaft is envisioned to be used to transmit motion in a curvilinear manner such as a catheter shaft delivered through the iliac arch in the hip region, or for use as a bone reamer with flexible medullary canal reamers.

Historically, flexible shafts have been comprised of braided wire, slotted tubing, wound wire, or small diameter polymer tubing. Small diameter polymer tubing is not considered an ideal option for some applications due to a lack of pushability and high risk of kinking. This ability to transmit energy from one end of the shaft to the other is considered one of the most important characteristics when maneuvering through long, tortuous vessels. Hypotube-based shafts with a slotted or spiral cut pattern can extend the traditional limits of metal shafts, but continue to present limitations with flexibility and torque transmission. The traditional spiral cut pattern, for example, tends to wind up when torqued such that a one revolution turn at the torqued, or proximal end does not equal a one revolution turn at the non-torqued or distal end; in the worst cases, a one revolution turn results in a less than one-quarter of a revolution or less. The standard slotted pattern with no or limited male-female portion has better torquability, but often limited bend radius along one or more planes.

Catheters and guidewires can include a full or portion of a shaft that is both flexible and torqueable or has a gradient of flexibility and torquability along the length of the shaft. For optimal steerability and pushability, most catheter designs must have a maximum torsional rigidity while retaining a satisfactory kink-resistance and flexibility. These shafts can be used in many catheters and introducers including those for balloon angioplasty, stent delivery, electrophysiology applications, drug delivery or infusion, atherectomy, crossing catheters, or endovascular surgery. Depending on the application, the optimized and gradation of the flexibility and torquability can be further modified by having a tube within a tube where the inside or outside tube or both can be comprised of a cut tube of this invention.

Chronic total occlusion (CTO) remains one of the most challenging pathologies encountered by surgeons and interventionalists alike. CTO is characterized by heavy atherosclerotic plaque burden resulting in complete, or near complete occlusion of a vessel for at least 1-3 months. CTO can occur in any part of the arterial vasculature, however, it is most common in the legs and other arteries near the heart. Chronic occlusions are present in up to 40% of patients who undergo treatment of symptomatic peripheral artery disease (PAD) and have been cited as one of the primary reasons for procedural failures. PAD is a prevalent condition, affecting about 10 million individuals in the United States and over 27 million individuals worldwide. CTO is also prolific in patients with coronary artery disease (CAD), the number one cause of death in the United States in both men and women, killing over 400,000 each year. Approximately 30% of all coronary angiograms in patients with coronary artery disease will show a CTO.

Restoring blood flow to the affected area is essential for improving blood supply and tissue perfusion to prevent limb amputation, heart failure and other clinical symptoms associated with these diseases. There are presently two predominate treatment strategies for CTO: bypass surgery or percutaneous recanalization. Until recently, CTOs of the coronary arteries were almost entirely referred for coronary artery bypass graft (CABG) procedures, or many were left untreated because of the high risk and uncertainty regarding CABG success rates. With a failure rate of up to 30%, recanalization poses its own set of technical challenges. A tough, fibrous cap is often present at the proximal and distal ends of the CTO with softer material in between. The majority of recanalization failures are due to an inability to cross the occlusion with the guidewire and balloon technologies currently available. Despite these challenges percutaneous revascularization has been associated with reduced angina, improved left ventricular function, reduced arrhythmias, and reduced mortality. Further innovations and refinement of current crossing catheter technologies are essential to increase procedural success in crossing long, calcified CTOs. Although the worst case for crossing a blocked vessel may be crossing one with a CTO, the intent of the invention is also for use for partial occlusions or simply crossing tortuous anatomy since the given construction can enable optimal performance in many applications.

SUMMARY

The invention provides a flexible, elongated catheter tube having distal and proximal ends and a laser cut section there between. The laser cut section makes up a majority of the catheter length and is cut in a continuous helical pattern forming interlocking teeth which can be sinusoidal, triangular, square or like shapes, preferably sinusoidal, wherein: (i) the interlocking teeth have a diameter of about 0.005 to about 0.015 inch, preferably from about 0.007 to about 0.015 inch; (ii) the helical angle of the center-line of the laser cut is a constant angle between about 64° and about 75°; (iii) the pitch between adjacent rows of teeth is in the range of about 0.028 to about 0.057 inch; (iv) the diameter of said teeth, the helical angle and the pitch resulting in from 4 to 12 repetitions of the teeth around the circumference of the laser cut section; and (v) the outside diameter of the tube is in the range of about 0.010 to about 0.052 inch and the wall thickness is about 0.001 to about 0.005, preferably 0.0015 inch.

The interior of the catheter tube has a polymeric bi-layer of a nylon or like polymer at the interface of the tube interior and a TEFLON® or like polymer forms the interior lumen of the catheter. The exterior of the tube has a thin polymer coating of nylon or the like.

The proximal end of the catheter is uncut and configured for coupling to a luer connection. A short portion of the distal end is also uncut and is followed by a narrower terminal section about 0.149 inch or less in length which can be tapered for better blockage penetration.

In operation, the interlocking teeth disengage and reengage in a fish-scale manner without undergoing significant plastic deformation and without substantial polymer separation when the catheter is flexed as it travels through a body lumen such as a blood vessel. The catheter is thus capable of transmitting an axial, push force against a vascular occlusion to cross same and allow the catheter to advance beyond the occlusion.

The invention also provides a process for resolving partial or total body lumen blockages or occlusions which includes inserting the catheter described above into body lumen having a blockage at a distal location and advancing the catheter through the body lumen until the distal end encounters the blockage. The interlocking teeth disengage and reengage in a fish-scale manner without undergoing plastic deformation and without substantial polymer separation when the catheter is flexed during advancement thru the body lumen. An axial push force is transmitted from the proximal end of the catheter to the distal end to cross the blockage and allow the catheter to advance there beyond.

The invention further provides a catheter tube which in cross section has an inside diameter of not less than about 0.010 inch, a polymeric bi-layer of a nylon polymer at the interface of the tube interior, a TEFLON® polymer forming the internal lumen of the catheter and a thin polymer exterior coating of a nylon or like polymer. The wall thickness of the catheter with inner layers and an outer coating is about 0.0015 to 0.010, preferably 0.007 inch.

BRIEF DESCRIPTION OF THE DRAWINGS

The invention will be more fully understood from the following description and drawings wherein:

FIG. 1 is a diagrammatic side view of a catheter tube with dimensions of a preferred embodiment by way of example (all dimensions are in inches unless noted otherwise);

FIG. 1A is an exploded side view of a portion of the cut pattern shown in FIG. 1 with dimensions of a preferred embodiment by way of example;

DETAILED DESCRIPTION OF SPECIFIC EMBODIMENTS

The catheter of the invention provides an unexpected and surprising combination of flexibility and the ability to deliver an axial push force greater than heretofore possible against an occlusion or total blockage to cross same and allow the catheter to advance there beyond. Flexibility allows an interventional radiologist using the inventive catheter to apply a twisting force or torque while pushing the catheter forward and follow a tortuous path in a body lumen (such as the iliac arch) without kinking. The distal section can be straight or angled as is known in the art.

Once kink-free delivery of the distal end to the point of a blockage or an occlusion is accomplished, the radiologist needs to apply axial pressure against the blockage to pass through or cross same to deliver a stent or other device to resolve the occlusion or blockage. For example, calcified lesions in an artery, known as chronic total occlusions (or CTOs) often have end caps that can be significantly harder to pierce or cross than the center of a CTO.

The catheter of the invention has demonstrated the ability to cross CTOs, even those with denser end caps, by exerting an axial push force in excess of 0.15 pounds and as high as one pound and more which is greater that heretofore possible with known catheters of comparable size. The inability to cross a CTO often leads to alternate and often riskier procedures (like open-heart surgery) to resolve a CTO.

The inventive catheter gives the radiologist several options for resolving a blockage. Once a guidewire locates a blockage, the inventive catheter can be inserted over the guidewire. A short section of the guidewire protruding from and supported by the catheter can challenge the CTO, or the distal end of the catheter and guidewire can be coextensive when pushed against a blockage or the guidewire can be withdrawn and the necked-down end of the catheter can be pushed through a CTO.

The structural parameters of the catheter of the invention are critical in achieving kink-free torquing and sufficient axial force to cross body lumen blockages. For example, the interlocking sinusoidal teeth must be able to disengage and reengage for flexibility without plastic deformation. Lesser values for teeth diameter and the pitch between rows of teeth can provide flexibility, and therefore better torque response around a bend, but at a cost of catheter buckling and decreased transmission of axial force. Exceeding the same values introduces undesirable stiffness and the inability to traverse tortuous body lumens. The use of interior and exterior polymer coatings (which may extend into, interface or blend with each other through the laser cut lines) aid in allowing the teeth to unlock (flex) and interlock without plastic deformation. Thus, smaller teeth may aid flexibility but easily deform; larger teeth resist unlocking and lead to undesirable stiffness.

Figure 6:
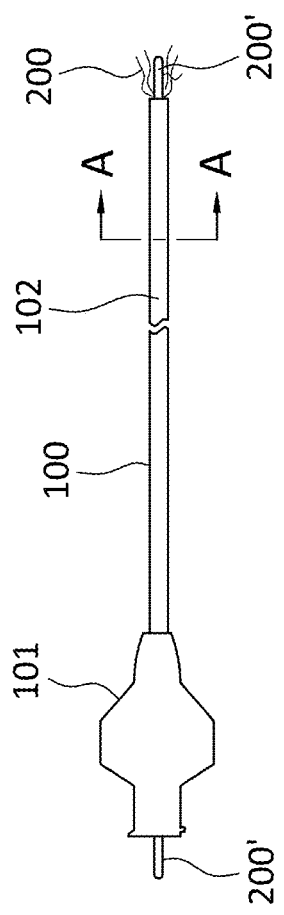
FIG. 6 is a schematic diagram of the catheter of FIG. 1 having a luer fitting-attached to the proximal end of the catheter to allow flushing of the catheter prior to use.

Referring now to the drawings, FIG. 6 shows the inventive catheter generally indicated at 100. Catheter 100 includes a laser cut catheter tube 102 having a luer fitting 101 attached at the proximal end thereof to allow flushing of the catheter prior to use. Catheter 100 is capable of accepting ancillary devices typically used in endovascular and related medical procedures such guidewire 200' which is used to track catheter 100 to the target treatment area in a body lumen or to inject contrast fluid 200 through the catheter to enable imaging during a procedure.

Figure 7:
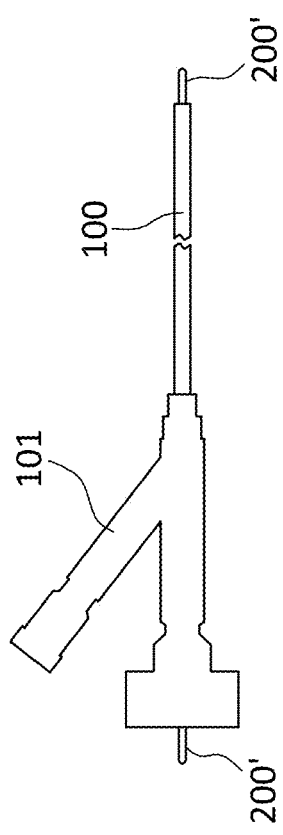
FIG. 7 is an alternate embodiment to FIG. 6 wherein the proximal luer is bifurcated to facilitate the delivery of multiple ancillary devices during a medical procedure.

FIG. 7 is similar to FIG. 6 wherein the proximal luer 101 is bifurcated to facilitate the delivery of multiple ancillary devices 200' through catheter 100 during a medical procedure.

Figure 4:
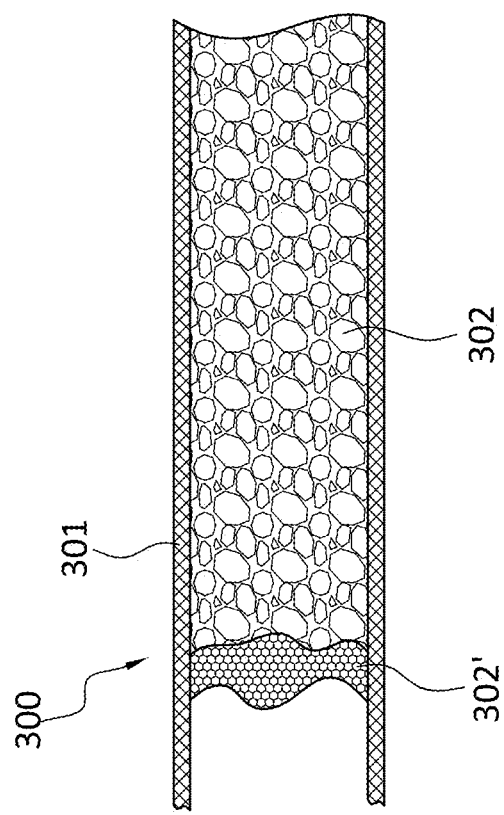
FIG. 4 is a schematic of a diseased artery with a total blockage including a denser end cap.

FIG. 4 shows a diseased artery 300 comprised of an arterial wall 301 and a heavily calcified lesion 302 known as a chronic total occlusion (CTO) which is typically comprised of denser end caps 302' on the proximal and distal ends that are significantly harder to access than the center of CTO 302.

Figure 5:
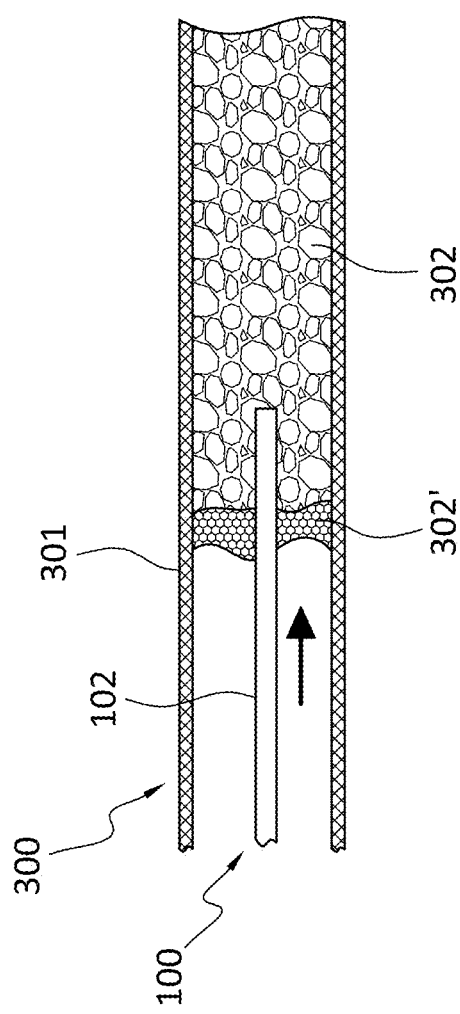
FIG. 5 is the same schematic as FIG. 4 showing a catheter of the invention crossing a dense end cap and entering the blockage.

FIG. 5 shows the distal end of catheter 100 crossing CTO 302 shown in FIG. 4. In order to cross the lesion, catheter 100 is capable of transmitting adequate force to the distal end when being pushed at the proximal and transmit adequate torque to the distal end when torque is applied to the proximal end. Catheter 100 is flexible enough at the distal end to navigate tortuous anatomies of the vasculature in order to reach the target site as well as be able to transmit force and torque in this configuration.

Figure 1B:
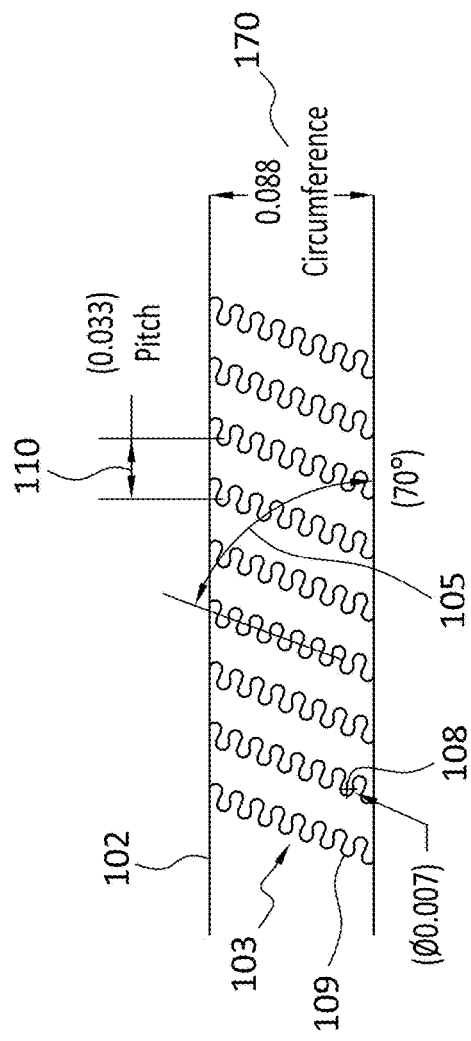
FIGS. 1B-1D are exploded side views of alternate cut patterns for use in the catheter of FIG. 1 with dimensions by way of example.
Figure 1C:
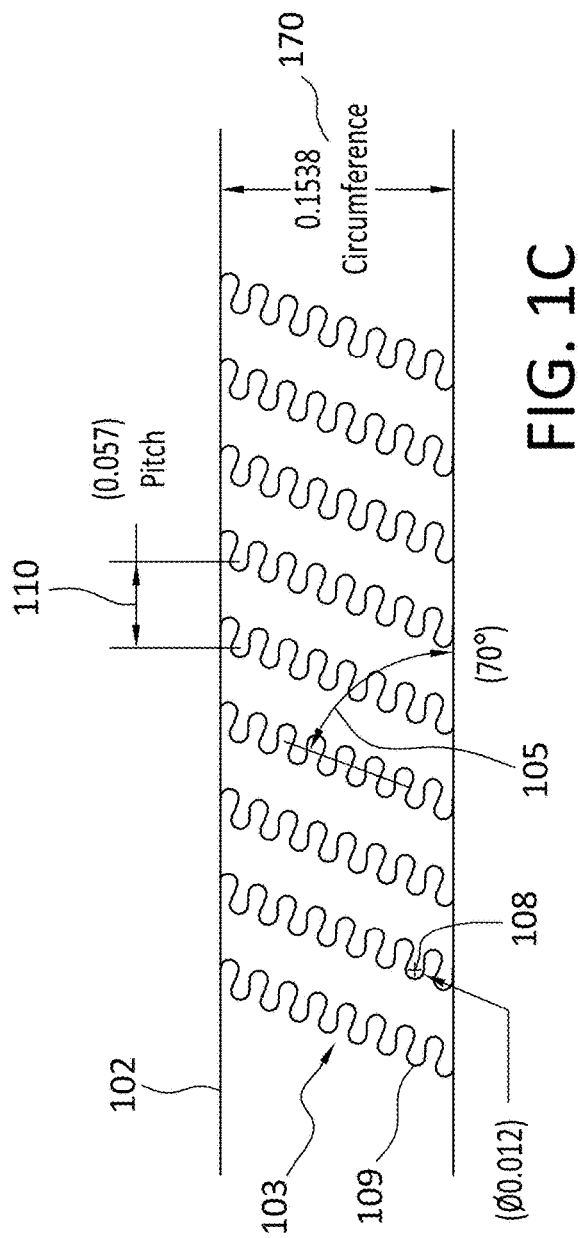
Figure 1D:
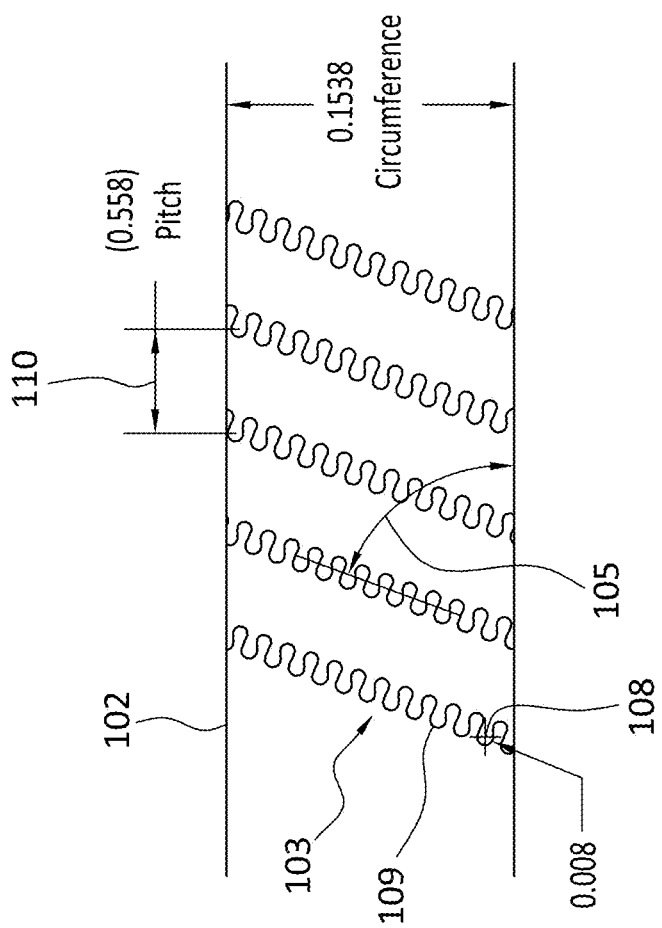
Figure 1E:
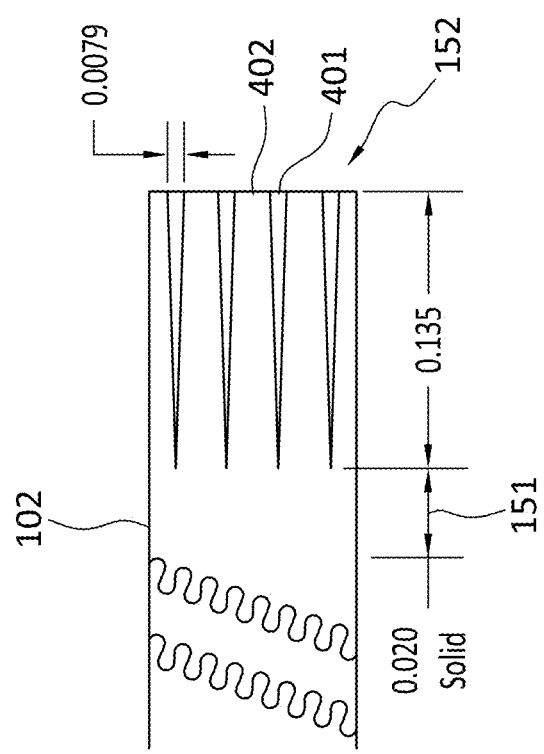
FIG. 1E is an exploded side view showing details of the distal end of the catheter of FIG. 1 with dimensions by way of example.
Figure 2:
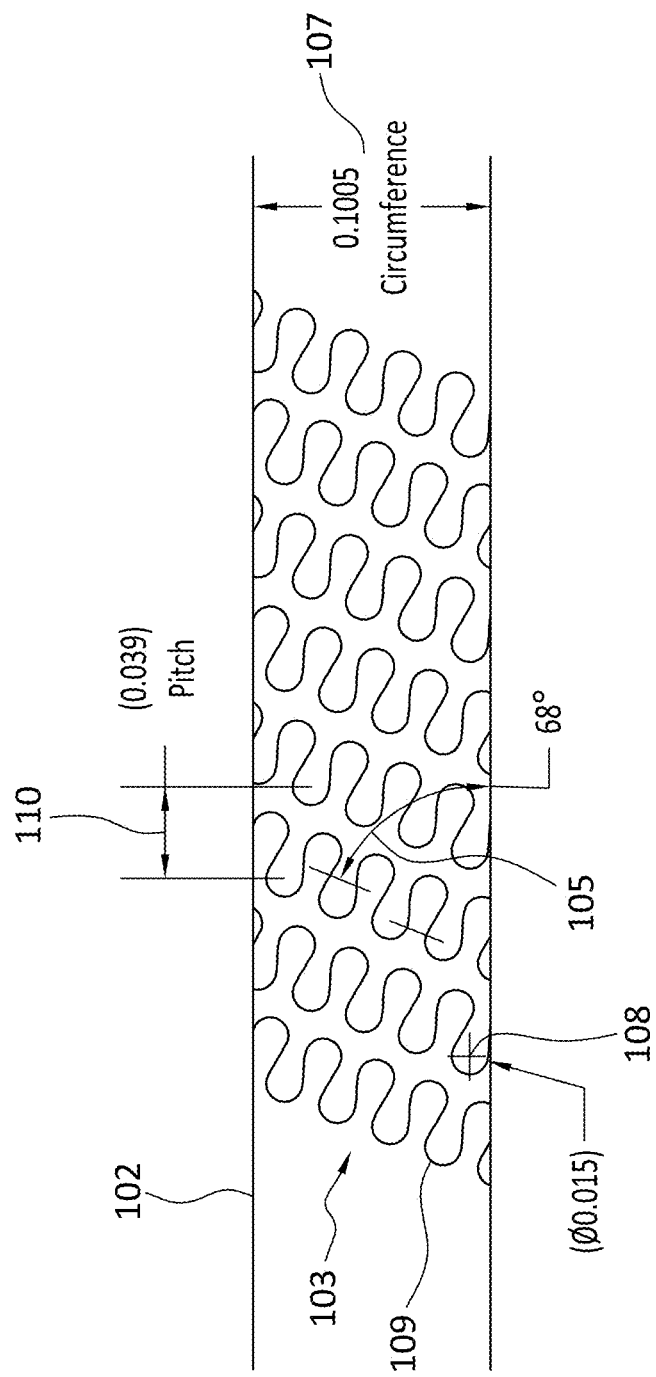
FIGS. 2 and 3 are exploded side views of alternate cut patterns for use in the catheter of FIG. 1 with dimensions by way of example.
Figure 3:
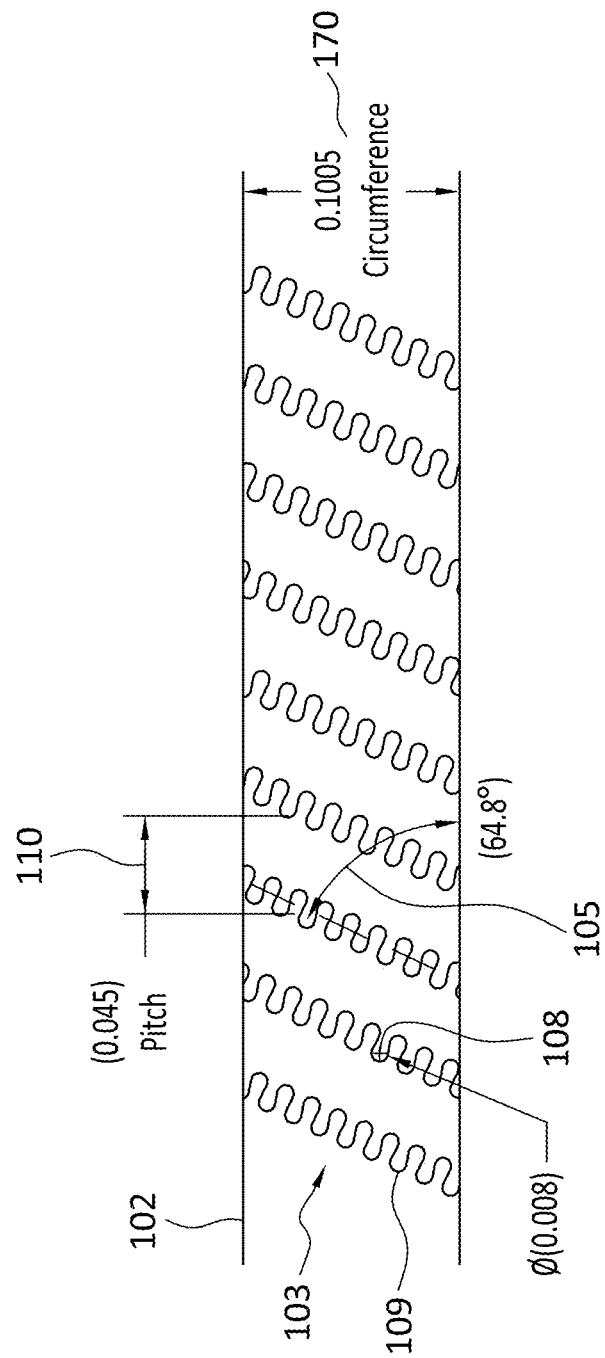

FIGS. 1, 1A and 1E show a preferred embodiment of catheter tube 102. The overall length 155 of tube 102 is shown for example as 61.3 inches, it being understood that solid section 157, shown as 8 inches in length, includes a portion which is gripped for laser cutting; end portion 157 is shortened considerably after laser cutting (to from 0.5 to 3 inches for example) for connection to a luer device as shown in FIGS. 6 and 7. The finished catheter 100 will typically have a length of 90, 135 or 170 cm, depending on the medical procedure being used.

FIG. 1 indicates two detail portions, the first at 156 for the tube cut pattern shown in FIG. 1A and the other at 158 for the distal end configuration shown in FIG. 1E. FIGS. 1A-1D and FIGS. 2 and 3 show alternate embodiments of the tube cut pattern with dimensions in each figure by way of example. Like elements have like reference numerals.

Figure 12:
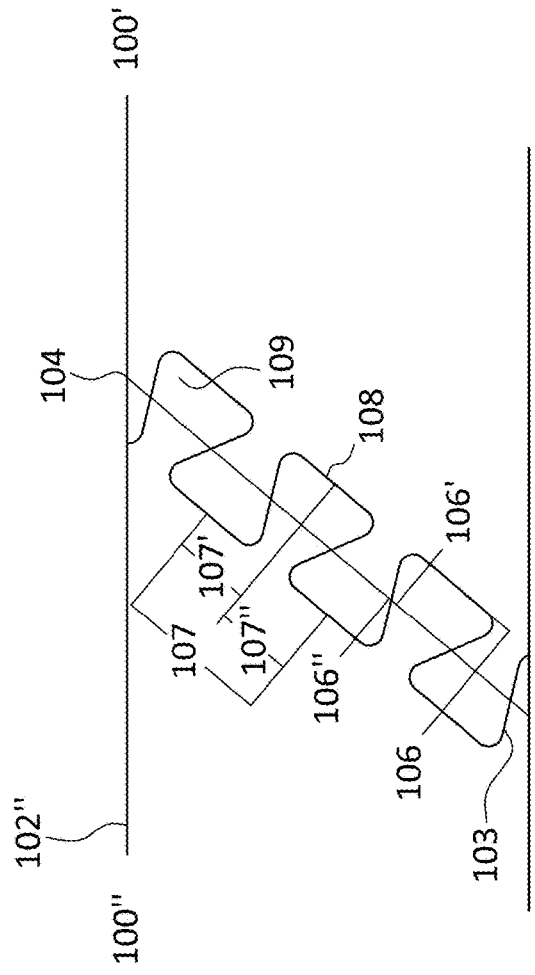
Figure 13:
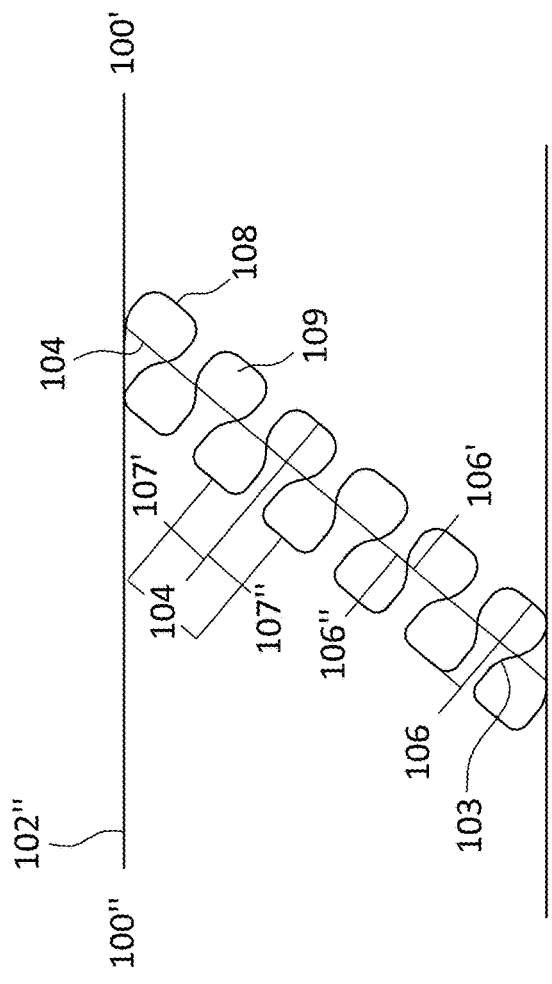

Tube 102 has distal and proximal ends 152 and 150, respectively, and a laser cut section 154 there between enabling the transmission of rotary and axial motion from the proximal end to the distal end. The laser cut section 154 comprises a majority, i.e., from about 90 to 95%, of the catheter length and is cut in a continuous helical pattern 103 forming interlocking sinusoidal shaped teeth 109 as shown in FIGS. 1A-1D, 2 and 3. The sinusoidal shape is preferred because it facilitates disengaging and reengaging of teeth 109 when the catheter is flexed. Other useful teeth shapes include triangular and square shapes as shown in FIGS. 12 and 13.

As shown in FIGS. 1A-1D, 2 and 3, sinusoidal teeth have a diameter 108 in the range from about 0.005 to about 0.015 inch and the helical angle 105 of the center-line of the sinusoidal cut 103 is a constant angle between about 64° and about 75°. The diameter of the interlocking sinusoidal teeth can also be expressed as a percentage of the diameter of tube 102, for example from about 5 to 15%, preferably about 8%, of the diameter of catheter tube 102.

The pitch 110 between adjacent rows of teeth 103 is in the range from about 0.028 to about inch. The diameter 108 of teeth 109, helical angle 105 and pitch 110 result in from 4 to 12 repetitions of teeth 109 around the circumference of laser cut section 154.

The outside diameter of tube 102 is in the range from about 0.010 to about 0.052 inch and the wall thickness is about 0.0015 to about 0.005 inch.

Figure 8B:
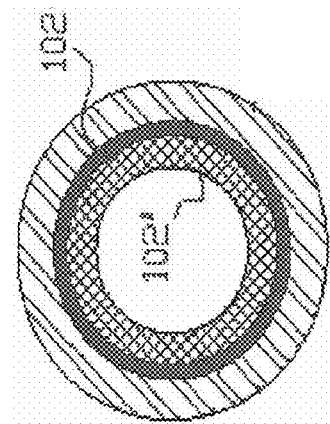
FIGS. 8A and 8B are alternate cross sections of a catheter of the invention with an inner polymer layer and an outer polymer sheath or coating.
Figure 8A:
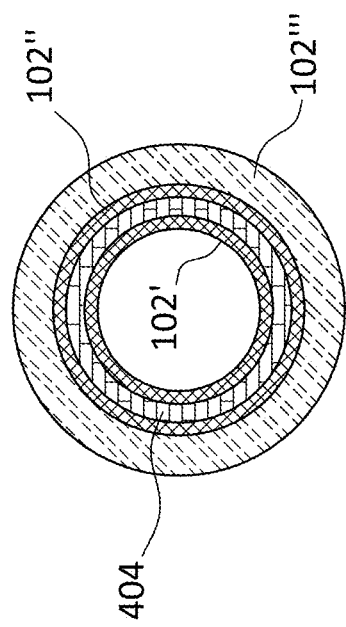

FIG. 8A shows the catheter of FIG. 1A in cross section having a polymeric bi-layer of a nylon or like polymer 404 at the interface of catheter tube 102 interior, a TEFLON® or like polymer 102' forming the internal lumen of the catheter, and a thin nylon or like polymer exterior coating 102'''. As an alternative, the cross section of FIG. 8B has a polymer layer 102' at the interface of catheter tube 102 interior forming the internal lumen of the catheter, and a polymer coating 102''' on the exterior.

Proximal end 150 (FIG. 1) comprises an uncut portion 157 configured for coupling to a luer connection (FIGS. 6 and 7). Distal end 152 (FIG. 1E) comprises a solid, uncut section no longer than about 0.02 inch followed by a narrower terminal section no longer than about 0.149 inch in length. Distal end 152 can be narrowed or necked down by compressing end segments 402 created by gusset cuts 401 (FIG. 1E).

In operation, interlocking teeth 109 disengage and reengage in a fish-scale manner without undergoing plastic deformation and without substantial polymer separation when the catheter is flexed. The catheter is thus capable of transmitting an axial push force against a vascular occlusion to cross same and allow the catheter to advance beyond the occlusion.

Figure 11:
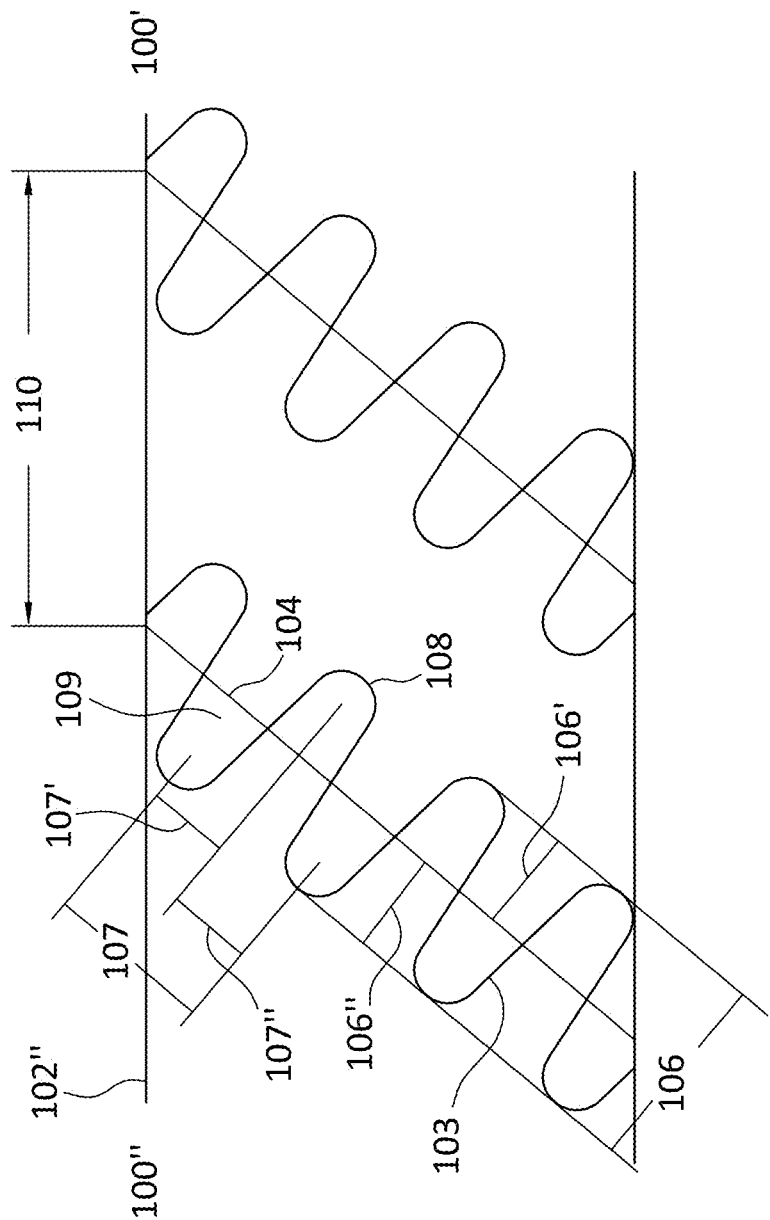
FIGS. 11-17 depict alternate cut patterns for forming interlocking teeth.

FIG. 11 is a schematic of the metallic tube of the middle layer 102" of the catheter shaft 102 having a distal end 100' and a proximal end 100". The middle metallic layer 102" is comprised of a helical sinusoidal cut pattern 103 drawn from a reference or center-line 104 that is on an angle 105 relative to the longitudinal length of the metallic tube 102". The path of the sinusoidal cut pattern has a peak-to-peak amplitude 106 and period 107. The peak-to-peak amplitude 106 of the cut pattern is split into an amplitude on the distal side of the center-line 106' and an amplitude on the proximal side of the center-line 106". Similarly, the period 107 is split into a distal period 107' and a proximal period 107" as illustrated in FIG. 11. The peaks and valleys of the sinusoidal cut path consist of a peak cut shape 108, which along with the period 107 creates teeth 109 between adjacent peaks or valleys. A pitch 110, the longitudinal spacing from center-line to center-line, is a function of the circumference of the metallic tube 102" and the center-line angle 105. The frequency is calculated by dividing the period 107 from the circumference of the metallic tubing 102".

FIG. 12 shows an alternate embodiment of the cut pattern in FIG. 11, in which the frequency is decreased and the peak cut shape 108 is primarily triangular. The peak cut shape 108 creates teeth 109 that effectively interlock the metallic tubing on the distal and proximal sides of the cut providing increased torque response of the catheter.

FIG. 13 shows an alternate embodiment of the cut pattern in FIG. 11, in which the frequency is increased and the peak cut shape 108 is primarily a square. The peak cut shape 108 creates teeth 109 that effectively interlock the metallic tubing on the distal and proximal sides of the cut providing increased torque response of the catheter.

Figure 14:
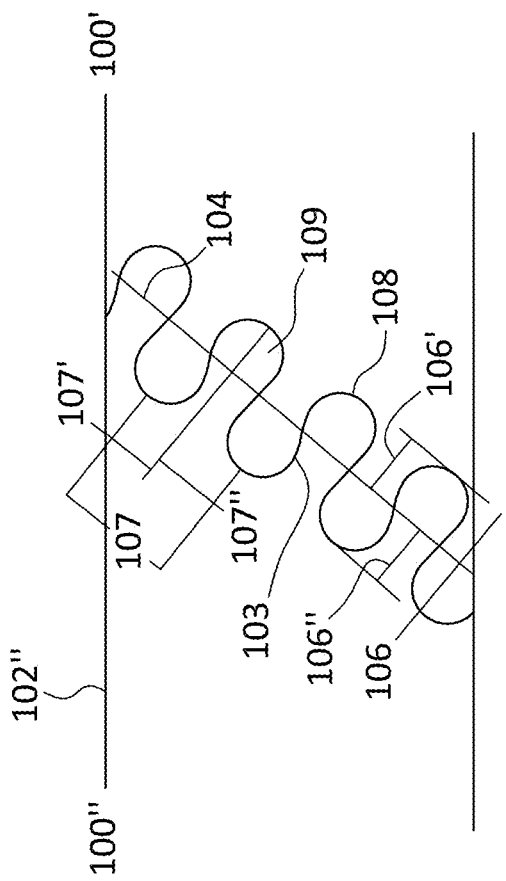

FIG. 14 shows an alternate embodiment of the cut pattern in FIG. 11, in which the distal period 107' and the proximal period 107" are not symmetric. Additionally, the peak cut shape 108 is drawn at a large diameter that along with the distal period dimension 107' creates teeth 109 between adjacent peaks and valleys that effectively interlock the metallic tubing on the distal and proximal sides of the sinusoidal cut providing increased torque response of the catheter.

Figure 15:
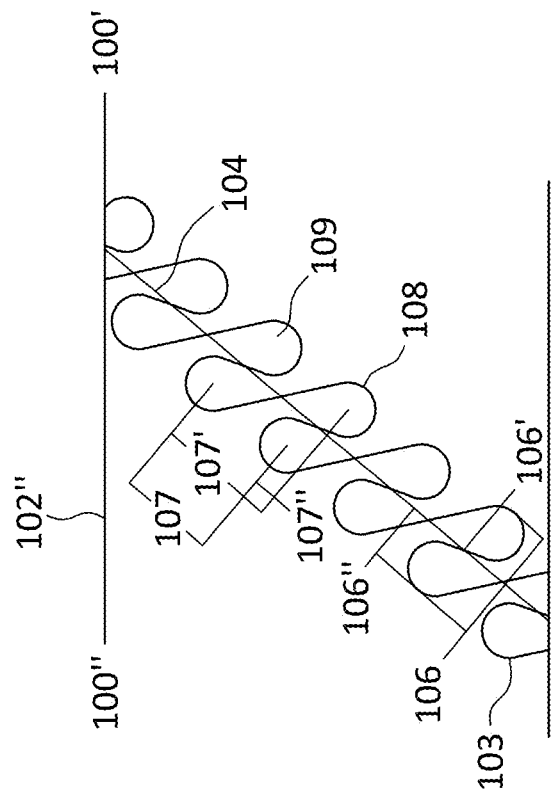

FIG. 15 shows an alternate embodiment of the cut pattern in FIG. 11 in which the distal period 107' is greater than the period 107 and the proximal period 107" is equal to the difference between the distal period 107' and the period 107. The shown cut pattern orients the interlocking features primarily in the circumferential direction instead of the longitudinal direction (as shown in previous schematics) to prevent fish-scaling or hinging of the teeth 109 when the catheter is wrapped around a tight bend.

Figure 16:
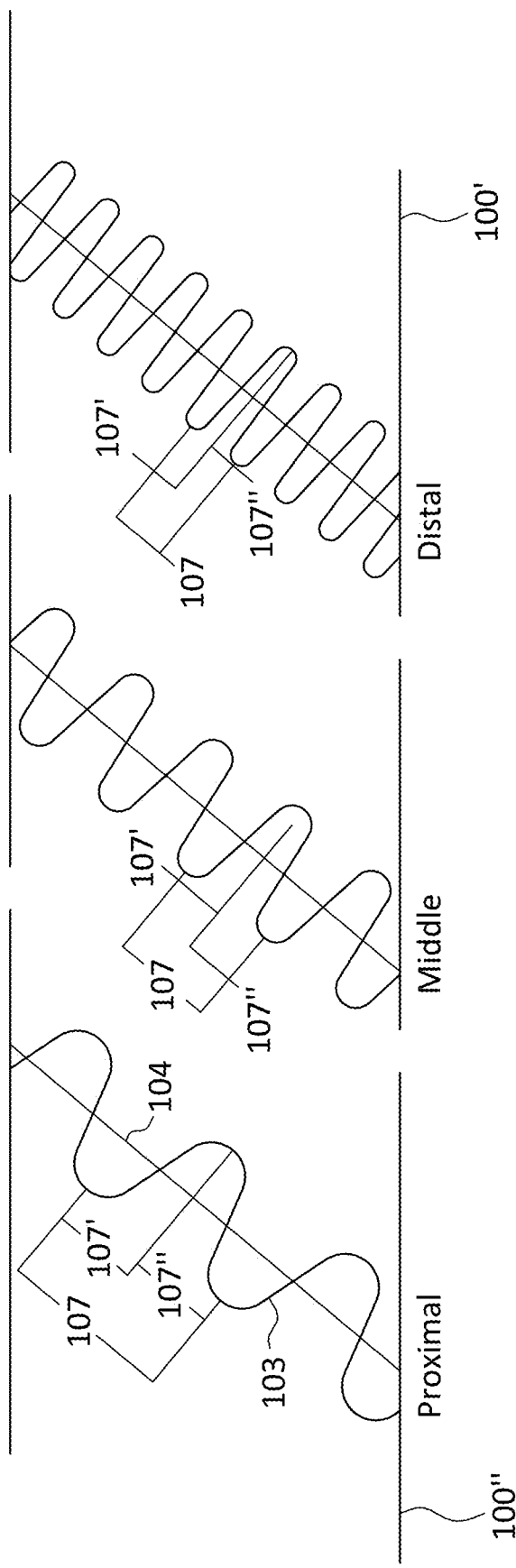

FIG. 16 shows a cut pattern 103, in which the period 107 decreases and the frequency increases along the length of the catheter from proximal 100" to distal 100'.

Figure 17:
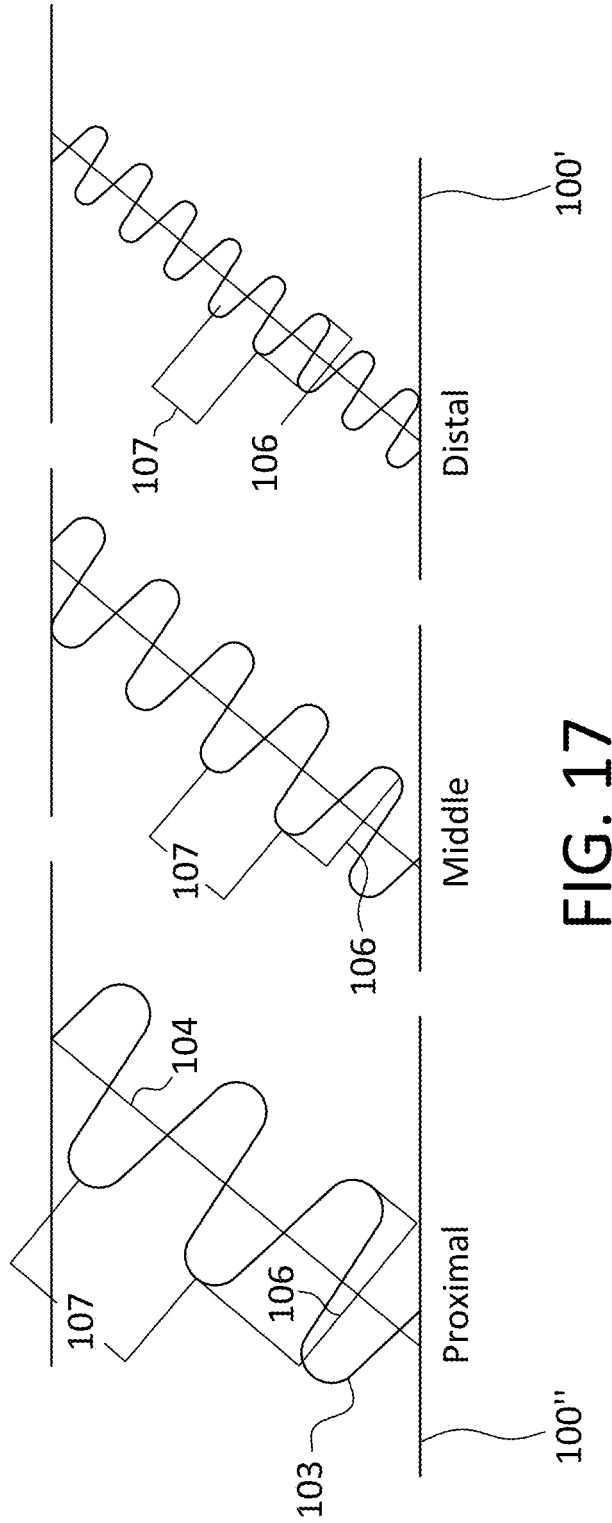

FIG. 17 shows a cut pattern 103, in which the period 107 and peak-to-peak amplitude 106 both decrease along the length of the catheter from proximal 100" to distal 100'.

The distal portions of the catheter can have a cutting feature or features which can be part of the catheter or a separate cannula that goes either over the outside diameter of the catheter or inside the diameter of the catheter.

A perfusion feature can be added to the catheter which enable the physician to flow liquid from the proximal end (outside of the body) to the distal end or a location or locations along the length of the catheter (FIGS. 6 and 7).

Another embodiment is a cut pattern similar to that shown in FIGS. 16 and 17 where the peak-to-peak amplitude 106 decreases while the period 107 remains constant.

In all embodiments, the helical angle could decrease or more likely increase from the proximal end to the distal end, or portions thereof including a center section. The helical angle shown in most drawings is 105 degrees, strictly as an example. Another example, the helical angle could start as 70 degrees and finish more distally at 112 degrees where the rate of angle change can be constant along the length or is variable. In all embodiments, the catheter can be used for CTO, partially blocked vessels, or other vessels or channels within a mammalian body. CTO is used as a difficult example or worst case under which the invention could need to perform if put into practice.

An important aspect of polymeric layers 102', 102''' and 404 (FIG. 8A) on both the inside diameter is the ability to greatly reduce "fish-scaling". Fish-scaling is the occurrence of a portion of a tube sticking out of surface of a bend or radius similar to how scales on a fish may protrude if the fish were bent at its half point in its body. Fish-scaling is an occurrence seen in stents that are not fully connected and can result in vessel damage. The reduction of fish-scaling can increase the torquability, flexibility or other attributes of a catheter depending on the tradeoffs decided in a given design. An interruption of the cover 102''' or a partial cover can allow an exit point or perfusion of a liquid. The material of cover 102''' can be a polymer or a polymer ceramic or a polymer with metal component such as heat shrunk TEFLON®, PEEK (polyether ether ketone), a combination of both, other like polymers and composites. The sealing or encapsulation material can be heat shrunk, sprayed or flowed onto cut tube 102. The material could also have some radiopaque materials added on some or all of the covering material.

A specific application of catheter 100 includes supporting a guidewire or catheter while crossing plaque buildup where the plaque creates a partial blockage or a total blockage also referred to as a chronic total occlusion (CTO).

Other applications which can use catheter 100 include bone reamers and shafts for many surgery devices requiring articulated segments.

EXAMPLES

Set of three catheters in the Table 1 were tested for flexibility and peak axial push force (lb f) and compared to commercially available catheters (described below) using simulation test apparatus shown in FIG. 9. Track tube 510 simulates the iliac arch and its five turns or bends at 510A-E. Track 510 is connected to bifurcated luer 512 for receiving catheter tube 100 which is fed over a guidewire into track 510 via traveling block 505 and tube 511 which carries collet 508 for gripping catheter 100 while it is pushed through track 510 by advancing block 505 via screw arm 506 which is driven by crank 507. Body temperature water is flowed over catheter tube 100 via water line 509 connected to luer 512. Peak push force is measure by pushing catheter 102 against pressure point 513' of load cell 513, Model MBD-100, and sent to digital reader Model SSI, both made by Transducer Techniques.

TABLE 1

| FIG. No. | Guidewire Compatibility | Outer Catheter Diameter | Tubing Wall Thickness |
|---|---|---|---|
| 1B | 0.014" | 2.9 Fr (0.038") | 0.0015" |
| 1A | 0.018" | 3.16 Fr (0.041") | 0.0015" |
| 1C | 0.035" | 4.46 Fr (0.059") | 0.00225" |
| 3 | 0.018" | 3.16 Fr (0.041") | 0.0015" |
| 2 | 0.018" | 3.16 Fr (0.041") | 0.0015" |

Formula for Scaling a Design:

$$(D_1/D_2)(T_1)=T_2$$

$D_1$=Diameter of desired tubing size
$D_2$=Diameter of current tubing size
$T_1$=Current tooth diameter
$T_2$=New tooth diameter $$(T_2/T_1)P_1=P_2$$

$T_1$=Current tooth diameter
$T_2$=New tooth diameter
$P_{-1}$=Current Pitch
$P_2$ New Pitch
Maintain cut angle
OR
Follow the above when scaling down, but when scaling up:
Maintain tooth diameter and cut angle
Increase number of repetitions:

$$(D_1/D_2)(R_1)=R_2$$

$D_1$=Diameter of desired tubing size
$D_{-2}$=Diameter of current tubing size
$R_1$=Current number of repetitions
$R_2$=New number of repetitions
Adjust pitch as necessary to create a continuous pattern.
Pushability Test Protocol
1) Track an appropriately sized guidewire through the simulated use model.

2) Flush the catheter with saline then track it over the guidewire through the simulated use model until the distal end is close to, but not contacting the load cell.
3) Retract the distal end of the guidewire about. 6" from the distal end of the simulated use model.
4) Clamp the system in place with the collet about. 1.5" from the entrance to the simulated use model and mark the system just distal to the collet to ensure it does not slip in the fixture during testing.
5) Zero the force gauge then rotate the crank arm until the load cell is preloaded to 0.05 lb+/−0.003.
6) Set the force gauge to peak and rotate the crank arm 3 full rotations (360° each). This constitutes one push. Each 360° rotation of the pusher arm translates the system ⅛" in the distal direction. Record the peak push force then rotate the arm 3 more times for push two and, again, record the peak force. Continue this method for 5 pushes or until the distal end of the system kinks.

Figure 9:
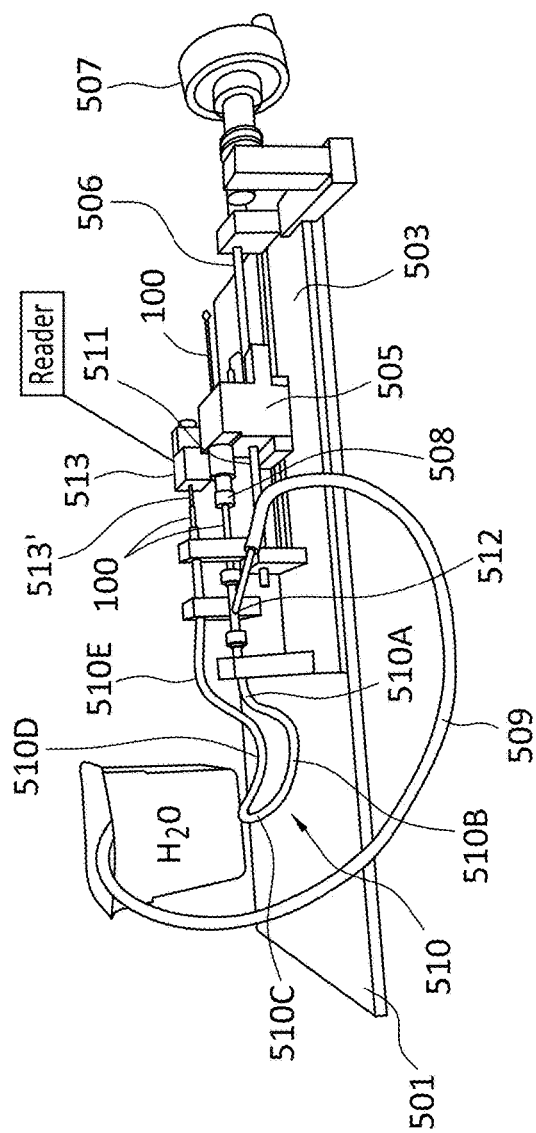
FIG. 9 is a perspective view of test apparatus used to ascertain flexibility and measure axial push force.

Commercial catheters, 3 of each design, were tested against the Table 1 catheters in the test apparatus of FIG. 9 following the same pushability protocol as above:

Control 1: A Cook CXI catheter which is a braided steel catheter (2.6 French) described as the MinaFlex 18 Microcatheter in a 510 (k) premarket notification summary submitted to the FDA by Cook International on Nov. 9, 2007 and available online from the FDA database (Ref. K072724).

Control 2: A Spectranetics Quick-Cross Support Catheter (2.1 French) which is a braided steel catheter described in a 510 (k) premarket notification summary submitted to the FDA by Spectranetics Corporation on Nov. 3, 2003 and available online from the FDA database (Ref. K033678).

Figure 18:
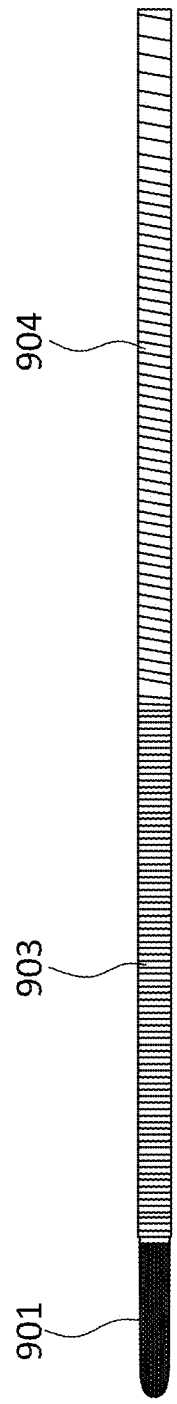
FIG. 18 is a sketch of a commercial catheter tested as a control against catheters of the invention.

Control 3: A Medtronic Total Across catheter which is a spiral cut stainless steel catheter (2.3 French) described in a 510 (k) premarket notification summary submitted to the FDA by Medtronic Vascular on Nov. 15, 2013 and available online from the FDA database (Ref. K133539) and depicted in FIG. 18 (drawn from a product brochure) with polymeric distal tip 901 and spiral windings 903 and 904.

Figure 10:
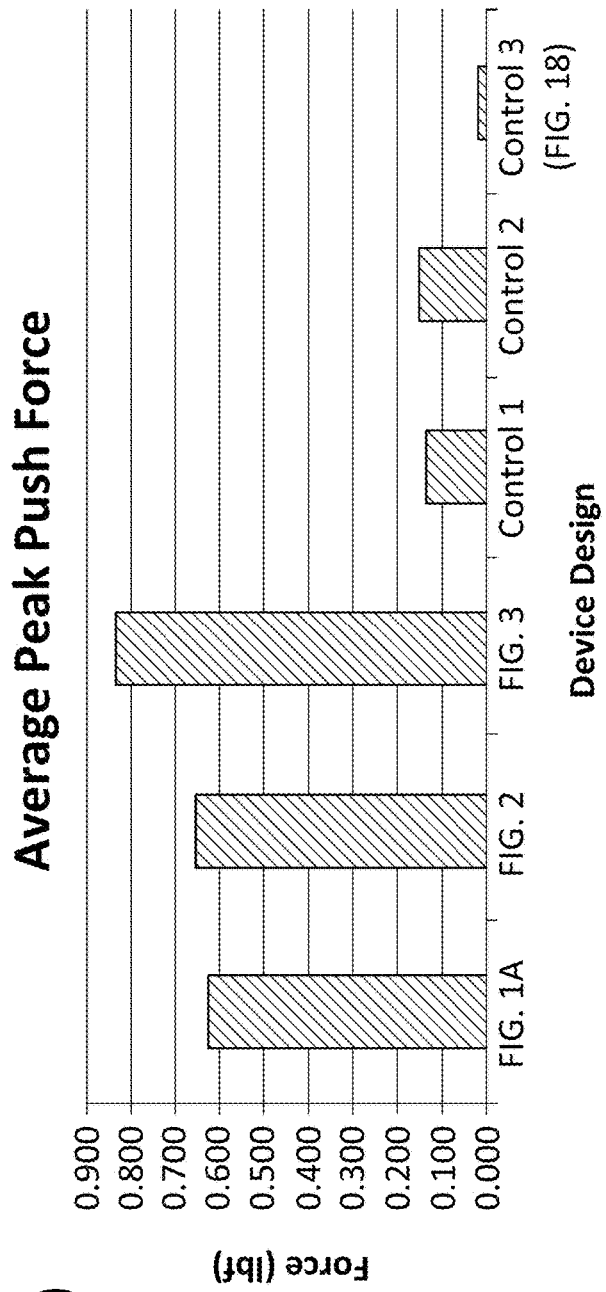
FIG. 10 is a bar graph of average peak push force measured with the test apparatus shown in FIG. 9.

Test results are summarized in the bar graph of FIG. 10 wherein catheters according to the invention (FIGS. 1A, 2 and 3) demonstrated average peak push force values on the order of 4 to 5 times higher than the control catheters.

While this invention has been described as having preferred sequences, ranges, ratios, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

We claim:

1. A process for resolving total or partial body lumen blockages, said process comprising:
   (a) inserting a catheter into a body lumen having a blockage,
      said catheter comprising an elongated tube having an exterior and an interior, an internal lumen, a distal end and a proximal end, and a laser cut section between said distal and proximal ends comprising substantially 90% to 99% of the length of said catheter, which is able to transmit rotary and axial motion from said proximal end to said distal end; wherein
      (i) said laser cut section comprises a continuous, uniform helical cut pattern having a constant cut angle forming rows of interlocking teeth with a constant pitch between adjacent rows of interlocking teeth, said helical cut pattern making from 4 to 12 repetitions around said catheter;
      (ii) said proximal end of the tube having a solid, uncut section;
      (iii) said distal end of the tube having a solid, uncut section;
      (iv) said tube interior has a polymer layer thereon and such interior polymer layer forms said internal lumen; and
      (v) said tube exterior has a polymer coating;
      whereby said catheter is able to flex without substantial separation of said polymer coating from the exterior; then
   (b) transmitting an axial push force from said distal end to said proximal end to cross the blockage and to advance said catheter beyond the blockage.

2. The process of claim 1 wherein said blockage is a chronic total occlusion.

3. The process of claim 2 wherein said chronic total occlusion has one or more hard end caps.

4. The process of claim 2 wherein said chronic total occlusion is without hard end caps.

5. The process of claim 1 wherein said interlocking teeth have a diameter in a range from 0.005 to 0.015 inch.

6. The process of claim 1 wherein said constant cut angle is between 64° and 75°.

7. The process of claim 1 wherein said constant pitch is from 0.033 to inch.

8. The process of claim 1 wherein said catheter has an outer diameter from 2.9 French (0.038 inch) to 4.46 French (0.059 inch).

* * * * *